US009446120B2

(12) United States Patent
Morishita et al.

(10) Patent No.: US 9,446,120 B2
(45) Date of Patent: Sep. 20, 2016

(54) DNA VACCINE

(75) Inventors: Ryuichi Morishita, Suita (JP);
Hironori Nakagami, Suita (JP);
Hiroshi Koriyama, Suita (JP); Futoshi Nakagami, Suita (JP); Natsuki Yoshida, Ibaraki (JP)

(73) Assignees: Osaka University, Suita (JP); Anges MG, Inc., Ibaraki (JP)

( * ) Notice: Subject to any disclaimer, the term of this patent is extended or adjusted under 35 U.S.C. 154(b) by 10 days.

(21) Appl. No.: 14/111,699

(22) PCT Filed: Apr. 13, 2012

(86) PCT No.: PCT/JP2012/060099
§ 371 (c)(1),
(2), (4) Date: Dec. 19, 2013

(87) PCT Pub. No.: WO2012/141280
PCT Pub. Date: Oct. 18, 2012

(65) Prior Publication Data
US 2014/0099335 A1 Apr. 10, 2014

(30) Foreign Application Priority Data

Apr. 15, 2011 (JP) ................................. 2011-091493
Oct. 14, 2011 (JP) ................................. 2011-227320

(51) Int. Cl.
*A61K 39/29* (2006.01)
*A61K 45/06* (2006.01)
*C07K 14/575* (2006.01)
*A61K 39/00* (2006.01)

(52) U.S. Cl.
CPC ......... *A61K 39/292* (2013.01); *A61K 39/0005* (2013.01); *C07K 14/575* (2013.01); *A61K 2039/53* (2013.01); *C07K 2319/00* (2013.01); *C12N 2730/10143* (2013.01); *C12N 2770/32434* (2013.01)

(58) Field of Classification Search
None
See application file for complete search history.

(56) References Cited

U.S. PATENT DOCUMENTS

| | | | |
|---|---|---|---|
| 5,721,138 A | 2/1998 | Lawn | |
| 6,512,161 B1 | 1/2003 | Rouy et al. | |
| 6,713,301 B1 | 3/2004 | Wang | |
| 7,745,606 B2* | 6/2010 | Dina et al. | 536/24.2 |
| 2003/0157479 A1 | 8/2003 | Bachmann et al. | |
| 2003/0175296 A1 | 9/2003 | Brown et al. | |
| 2012/0157513 A1* | 6/2012 | Li et al. | 514/44 R |
| 2014/0086944 A1 | 3/2014 | Kyutoku et al. | |

FOREIGN PATENT DOCUMENTS

| | | |
|---|---|---|
| CN | 1201819 C | 5/2005 |
| CN | 1706502 A | 12/2005 |
| CN | 1896094 A | 1/2007 |
| CN | 101015689 A | 8/2007 |
| CN | 102247604 A | 11/2011 |
| JP | 3228737 B2 | 9/2001 |
| JP | 2002-500039 A | 1/2002 |
| JP | 2005-514333 A | 5/2005 |
| WO | WO 99/15655 A1 | 4/1999 |
| WO | WO 01/98333 A2 | 12/2001 |
| WO | WO 03/031466 A2 | 4/2003 |

OTHER PUBLICATIONS

Ambuhl et al., *Journal of Hypertension*, 25(1): 63-72 (2007).
Clarke et al., *Nature*, 330: 381-384 (1987).
Do et al., *Expert Opin. Biol. Ther.*, 10(7): 1077-1087 (2010).
Mao et al., *Vaccine*, 24: 4942-4950 (2006).
Marshall et al., *Journal of Leukocyte Biology*, 82: 497-508 (2007).
Schodel et al., *Journal of Virology*, 66(1) 106-114 (1992).
Schodel et al., *The Journal of Experimental Medicine*, 180: 1037-1046 (1994).
Tissot et al., *Lancet*, 371: 821-827 (2008).
Whiteacre et al., *Expert Rev. Vaccines*, 8(11): 1565-1573 (2009).
Japanese Patent Office, International Search Report in International Patent Application No. PCT/JP2012/060099 (Jul. 17, 2012).
Chinese Patent Office, Office Action in Chinese Patent Application No. 201280027097.4 (Oct. 10, 2014).
Berg, Kare, *Acta Pathologica Microbiologica Scandinavica*, 59: 369-382 (1963).
Brown et al., *New England Journal of Medicine*, 323: 1289-1298 (1990).
Eaton et al., *Proc. Natl. Acad. Sci. USA*, 84: 3224-3228 (1987).
Ishii et al., *Nature*, 451: 725-729 (2008).
Kyutoku et al., "The Challenge for Apolipoprotein(a) DNA Vaccine as a New Therapeutic Strategy for Patients with Elevated Serum Lipoprotein(a) Level," Japan Atherosclerosis Society, Program & Proceedings, Abstract for Poster Session HS-7, pp. 59-60 and 197 (Jul. 19, 2012).
Kyutoku et al., "The Challenge for Apolipoprotein(a) DNA Vaccine as a New Therapeutic Strategy for Patients with Elevated Serum Lipoprotein(a) Level," The 44th Annual Scientific Meeting of the Japan Atherosclerosis Society, Poster Session HS-7 at the Hilton Fukuoka Sea Hawk Hotel in Fukuoka, Japan (Jul. 19, 2012).
McLean et al., *Nature*, 330: 132-137 (1987).
Miles et al., *Nature*, 339(6222): 301-303 (1989).
Morgan et al., *Nature*, 408: 982-985 (2000).
Nakagami et al., *Atherosclerosis*, 211: 41-47 (2010).
Nakagami et al., "Development of dyslipidemia DNA vaccine system for Lipoprotein(a)," Japan Society of Gene Therapy, 18th Annual Meeting Program, Program, Identity of Poster Session PO-78, pp. 21-23 [obtained from internet URL: http://jsgt.jp] (Jun. 28-30, 2012).

(Continued)

*Primary Examiner* — Agnieszka Boesen
(74) *Attorney, Agent, or Firm* — Leydig, Voit & Mayer, Ltd.

(57) ABSTRACT

The present invention provides a therapeutic or improving agent for a lifestyle-related disease, containing an expression vector encoding a chimeric Hepatitis B virus core antigen polypeptide inserted with an amino acid sequence containing a specific epitope of the lifestyle-related disease-related factor, wherein the amino acid sequence containing the specific epitope is inserted between the amino acid residues 80 and 81 of the hepatitis B virus core antigen polypeptide.

11 Claims, 3 Drawing Sheets

(56) References Cited

OTHER PUBLICATIONS

Nakagami et al., "Development of dyslipidemia DNA vaccine system for Lipoprotein(a)," Japan Society of Gene Therapy, 18$^{th}$ Annual Meeting Program, Program & Abstracts, Abstract for Poster Session PO-78, pp. 21-22 and 175 (Jun. 28-30, 2012).

Nakagami et al., "Development of dyslipidemia DNA vaccine system for Lipoprotein(a)," The 18$^{th}$ Annual Meeting of the Japan Society of Gene Therapy, Poster Session PO-78 at the Hotel Kumamoto Terrsa in Kumamoto, Japan (Jun. 28-30, 2012).

Scanu et al., *Journal of Clinical Investigation*, 85: 1709-1715 (1990).

Schenk, Dale, Nat. Rev. *Neuroscience*, 3: 824-828 (2002).

Taylor et al., *The New England Journal of Medicine*, 361: 2113-2122 (2009).

Yamada et al., *Clinica Chimica Acta*, 287: 29-43 (1999).

Koriyama et al., "Long Term Blood Pressure Reduction by Angiotensin II DNA Vaccine in Spontaneously Hypertensive Rats Model," abstract of Presentation 16969 at American Heart Association Symposium at Dallas, Texas (Nov. 18, 2013).

Nakagami et al., *International Heart Journal*, 55(2): 96-100 (2014).

Nakagami et al., *Journal of Cardiac Failure*, 20(10), S151, Abstract O-037 (2014).

European Patent Office, Extended European Search Report in European Patent Application No. 12771621.5 (Dec. 22, 2014).

U.S. Appl. No. 14/032,804, filed Sep. 20, 2013.

U.S. Appl. No. 15/201,029, filed Jul. 1, 2016.

Wigren et al., *Journal of Internal Medicine*, 269: 546-556 (2010).

\* cited by examiner

SEQUENCE LISTING

```
<160> NUMBER OF SEQ ID NOS: 31

<210> SEQ ID NO 1
<211> LENGTH: 556
<212> TYPE: DNA
<213> ORGANISM: Hepatitis B virus
<220> FEATURE:
<221> NAME/KEY: CDS
<222> LOCATION: (2)..(553)

<400> SEQUENCE: 1 c atg gat atc gat cct tat aaa gaa ttc gga gct act gtg gag tta ctc      49
  Met Asp Ile Asp Pro Tyr Lys Glu Phe Gly Ala Thr Val Glu Leu Leu
  1               5                   10                  15 tcg ttt ctc ccg agt gac ttc ttt cct tca gta cga gat ctt ctg gat        97
Ser Phe Leu Pro Ser Asp Phe Phe Pro Ser Val Arg Asp Leu Leu Asp
                20                  25                  30 acc gcc agc gcg ctg tat cgg gaa gcc ttg gag tct cct gag cac tgc       145
Thr Ala Ser Ala Leu Tyr Arg Glu Ala Leu Glu Ser Pro Glu His Cys
            35                  40                  45 agc cct cac cat act gcc ctc agg caa gca att ctt tgc tgg ggg gag       193
Ser Pro His His Thr Ala Leu Arg Gln Ala Ile Leu Cys Trp Gly Glu
        50                  55                  60 ctc atg act ctg gcc acg tgg gtg ggt gtt aac ttg gaa gat cca gct       241
Leu Met Thr Leu Ala Thr Trp Val Gly Val Asn Leu Glu Asp Pro Ala
65                  70                  75                  80 agc agg gac ctg gta gtc agt tat gtc aac act aat atg ggt tta aag       289
Ser Arg Asp Leu Val Val Ser Tyr Val Asn Thr Asn Met Gly Leu Lys
                85                  90                  95 ttc agg caa ctc ttg tgg ttt cac att agc tgc ctc act ttc ggc cga       337
Phe Arg Gln Leu Leu Trp Phe His Ile Ser Cys Leu Thr Phe Gly Arg
                100                 105                 110 gaa aca gtt cta gaa tat ttg gtg tct ttc gga gtg tgg atc cgc act       385
Glu Thr Val Leu Glu Tyr Leu Val Ser Phe Gly Val Trp Ile Arg Thr
            115                 120                 125
```

```
cct cca gct tat agg cct ccg aat gcc cct atc ctg tcg aca ctc ccg      433
Pro Pro Ala Tyr Arg Pro Pro Asn Ala Pro Ile Leu Ser Thr Leu Pro
    130                 135                 140 gag act act gtt gtt aga cgt cga ggc agg tca cct aga aga aga act      481
Glu Thr Thr Val Val Arg Arg Arg Gly Arg Ser Pro Arg Arg Arg Thr
145                 150                 155                 160 cct tcg cct cgc agg cga agg tct caa tcg ccg cgg cgc cga aga tct      529
Pro Ser Pro Arg Arg Arg Arg Ser Gln Ser Pro Arg Arg Arg Arg Ser
                165                 170                 175 caa tct cgg gaa tct caa tgt tag tga                                  556
Gln Ser Arg Glu Ser Gln Cys
            180

<210> SEQ ID NO 2
<211> LENGTH: 183
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 3
<211> LENGTH: 185
<212> TYPE: PRT
<213> ORGANISM: Hepatitis B virus

<400> SEQUENCE: 3

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
```

```
                50                  55                  60
Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Asn Ala Pro Ile Leu Ser Thr Leu Pro
        130                 135                 140

Glu Thr Thr Val Val Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 4
<211> LENGTH: 11
<212> TYPE: PRT
<213> ORGANISM: Artificial Sequence
<220> FEATURE:
<223> OTHER INFORMATION: Synthetic Ang II epitope

<400> SEQUENCE: 4

Cys Gly Gly Asp Arg Val Tyr Ile His Pro Phe
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Ang II epitope

<400> SEQUENCE: 5

Cys Gly Gly Asp Arg Val Tyr Ile His Pro Phe His Leu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Ang II epitope

<400> SEQUENCE: 6

Asp Arg Val Tyr Ile His Pro Phe His Leu Gly Gly Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Ang II epitope

<400> SEQUENCE: 7

Cys Asp Arg Val Tyr Ile His Pro Phe His Leu
1               5                   10
```

```
<210> SEQ ID NO 8
<211> LENGTH: 6
<212> TYPE: PRT
<213> ORGANISM: Artificial Sequence
<220> FEATURE:
<223> OTHER INFORMATION: Synthetic Ang II eptitope

<400> SEQUENCE: 8

Cys His Pro Phe His Leu
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Ang II epitope

<400> SEQUENCE: 9

Cys Gly Pro Phe His Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Ang II epitope

<400> SEQUENCE: 10

Cys Tyr Ile His Pro Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Sytnthetic Ang II epitope

<400> SEQUENCE: 11

Cys Gly Ile His Pro Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Ang II epitope

<400> SEQUENCE: 12

Cys Gly Gly His Pro Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Ang II epitope

<400> SEQUENCE: 13

Cys Arg Val Tyr Ile Gly Gly Cys
1               5

<210> SEQ ID NO 14
```

```
<211> LENGTH: 7
<212> TYPE: PRT
<213> ORGANISM: Artificial Sequence
<220> FEATURE:
<223> OTHER INFORMATION: Synthetic Ang II epitope

<400> SEQUENCE: 14

Asp Arg Val Tyr Gly Gly Cys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Ang II epitope

<400> SEQUENCE: 15

Asp Arg Val Gly Gly Cys
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Ang II epitope

<400> SEQUENCE: 16

Asp Arg Val Tyr Ile His Pro Phe
1               5

<210> SEQ ID NO 17
<211> LENGTH: 25
<212> TYPE: PRT
<213> ORGANISM: Artificial Sequence
<220> FEATURE:
<223> OTHER INFORMATION: Synthetic CETP epitope

<400> SEQUENCE: 17

Arg Asp Gly Phe Leu Leu Leu Gln Met Asp Phe Gly Phe Pro Glu His
1               5                   10                  15

Leu Leu Val Asp Phe Leu Gln Ser Leu
            20                  25

<210> SEQ ID NO 18
<211> LENGTH: 22
<212> TYPE: DNA
<213> ORGANISM: Artificial Sequence
<220> FEATURE:
<223> OTHER INFORMATION: Synthetic CpG-B 1018

<400> SEQUENCE: 18
tgactgtgaa cgttcgagat ga                                          22

<210> SEQ ID NO 19
<211> LENGTH: 20
<212> TYPE: DNA
<213> ORGANISM: Artificial Sequence
<220> FEATURE:
<223> OTHER INFORMATION: Synthetic CpG-A D19

<400> SEQUENCE: 19
ggtgcatcga tgcagggggg                                             20

<210> SEQ ID NO 20
```

```
<211> LENGTH: 21
<212> TYPE: DNA
<213> ORGANISM: Artificial Sequence
<220> FEATURE:
<223> OTHER INFORMATION: Synthetic Ang II epitope

<400> SEQUENCE: 20
tcgtcgaacg ttcgagatga t                                              21

<210> SEQ ID NO 21
<211> LENGTH: 25
<212> TYPE: DNA
<213> ORGANISM: Artificial Sequence
<220> FEATURE:
<223> OTHER INFORMATION: Synthetic CpG-C C695

<400> SEQUENCE: 21
tcgaacgttc gaacgttcga acgtt                                          25

<210> SEQ ID NO 22
<211> LENGTH: 88
<212> TYPE: DNA
<213> ORGANISM: Artificial Sequence
<220> FEATURE:
<223> OTHER INFORMATION: Synthetic ISS

<400> SEQUENCE: 22
ggtgcatcga tgcaggggggg tgactgtgaa cgttcgagat gatcgtcgaa cgttcgagat   60
gattcgaacg ttcgaacgtt cgaacgtt                                       88

<210> SEQ ID NO 23
<211> LENGTH: 35
<212> TYPE: DNA
<213> ORGANISM: Artificial Sequence
<220> FEATURE:
<223> OTHER INFORMATION: Synthetic HBcF primer

<400> SEQUENCE: 23
gccatggata tcgatcctta taaagaattc ggagc                               35

<210> SEQ ID NO 24
<211> LENGTH: 36
<212> TYPE: DNA
<213> ORGANISM: Artificial Sequence
<220> FEATURE:
<223> OTHER INFORMATION: Synthetic HBcR primer

<400> SEQUENCE: 24
ggcctctcac taacattgag attcccgaga ttgaga                              36

<210> SEQ ID NO 25
<211> LENGTH: 48
<212> TYPE: DNA
<213> ORGANISM: Artificial Sequence
<220> FEATURE:
<223> OTHER INFORMATION: Synthetic H2 primer

<400> SEQUENCE: 25
ggggtggatg tatacgcggt cagtgatagc tggatcttcc aagttaac                 48

<210> SEQ ID NO 26
<211> LENGTH: 49
<212> TYPE: DNA
<213> ORGANISM: Artificial Sequence
<220> FEATURE:
<223> OTHER INFORMATION: Synthetic H3-II primer
```

<400> SEQUENCE: 26
ccgcgtatac atccacccct ttggtgctac tagcagggac ctggtagtc        49

<210> SEQ ID NO 27
<211> LENGTH: 13
<212> TYPE: PRT
<213> ORGANISM: Artificial Sequence
<220> FEATURE:
<223> OTHER INFORMATION: Synthetic inserted peptide

<400> SEQUENCE: 27

Ile Thr Asp Arg Val Tyr Ile His Pro Phe Gly Ala Thr
1               5                   10

<210> SEQ ID NO 28
<211> LENGTH: 88
<212> TYPE: DNA
<213> ORGANISM: Artificial Sequence
<220> FEATURE:
<223> OTHER INFORMATION: Synthetic CpG primer F

<400> SEQUENCE: 28
ggtgcatcga tgcaggggg tgactgtgaa cgttcgagat gatcgtcgaa cgttcgagat    60
gattcgaacg ttcgaacgtt cgaacgtt                                      88

<210> SEQ ID NO 29
<211> LENGTH: 88
<212> TYPE: DNA
<213> ORGANISM: Artificial Sequence
<220> FEATURE:
<223> OTHER INFORMATION: Synthetic CpG primer R

<400> SEQUENCE: 29
aacgttcgaa cgttcgaacg ttcgaatcat ctcgaacgtt cgacgatcat ctcgaacgtt    60
cacagtcacc cccctgcatc gatgcacc                                       88

<210> SEQ ID NO 30
<211> LENGTH: 28
<212> TYPE: DNA
<213> ORGANISM: Artificial Sequence
<220> FEATURE:
<223> OTHER INFORMATION: SyntheticDra III primer F

<400> SEQUENCE: 30
tttcacgtag tgggtgcatc gatgcagg                                       28

<210> SEQ ID NO 31
<211> LENGTH: 28
<212> TYPE: DNA
<213> ORGANISM: Artificial Sequence
<220> FEATURE:
<223> OTHER INFORMATION: Synthetic Dra III primer R

<400> SEQUENCE: 31
ggtcactacg tgaacgttcg aacgttcg                                       28

DNA VACCINE

CROSS-REFERENCE TO RELATED APPLICATIONS

This patent application is the U.S. national phase of International Patent Application No. PCT/JP2012/060099, filed Apr. 13, 2012, which claims the benefit of Japanese Patent Application No. 2011/091493, filed on Apr. 15, 2011, and Japanese Patent Application No. 2011/227320, filed on Oct. 14, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 12,166 bytes ASCII (Text) file named "714411SequenceListing.txt," created Oct. 14, 2013.

TECHNICAL FIELD

The present invention relates to a DNA vaccine effective for the treatment or prophylaxis of lifestyle-related diseases such as hypertension and the like.

BACKGROUND ART

It has been reported that, of the hypertension patients in US, only 35% can appropriately control the blood pressure. One of the major causes of such poor achievements of the hypertension treatment is patients' disobedience (namely, non-compliance) to the instruction of the doctors. As a therapy capable of solving the problem of non-compliance, vaccine for hypertension is drawing attention (non-patent document 1).

Vaccine for hypertension is a therapeutic method for hypertension including administering an aggravation factor of hypertension, an epitope contained in the aggravation factor, or an expression vector encoding them to hypertension patients to induce an antibody to the aggravation factor in the body of the hypertension patients, thereby neutralizing the function of the aggravation factor and mitigating the symptoms of hypertension. Various factors including rennin, angiotensin II and AT-1 receptor are proposed as the target of vaccine (non-patent document 1).

However, the immune tolerance to factors such as renin, angiotensin II, AT-1 receptor and the like has generally been established since these factors are the patient's own component. Therefore, it is difficult to induce an antibody to the factor in the body of the patient even when these factors or partial peptides thereof are directly administered to the patient. As such, some technical idea is necessary to have the patient's immune system recognize these self-antigens, thereby inducing the production of the antibody thereto.

Hepatitis B virus core (HBc) antigen protein constitutes spherical core particles by self-assembly. The core particles have very high immunogenicity. When a fusion polypeptide obtained by inserting a desired epitope into a particular site of the HBc antigen protein, or connecting a desired epitope to the terminus of the HBc antigen protein is used, the epitope is presented on the surface of the particles formed by self-assembly. Using the fusion polypeptide, the inserted epitope is easily recognized by the immune system, and the production of the antibody that recognizes the epitope can be efficiently induced. Therefore, utilizing the HBc antigen protein as a platform of vaccine, attempts have been made to induce production of the antibody even though an antigen is difficult to be recognized by the immune system (non-patent document 2, non-patent document 3).

Patent document 1 discloses particles composed of a chimeric HBc antigen protein containing a foreign amino acid sequence having an epitope, wherein the foreign amino acid sequence is inserted between the amino acid residues 80-81 of the HBc antigen.

Patent document 2 and non-patent document 4 disclose complexes containing partial peptide of angiotensin II, spacer and virus-like particles (VLP), wherein the partial peptide of angiotensin II is connected to VLP via the spacer. It is described that the complex is useful as a vaccine for hypertension.

Patent document 3 discloses an immunogenic polypeptide obtained by inserting a cholesteryl ester transfer protein (CETP) immunogen to a particular region of Hepatitis B core protein.

Non-patent document 5 discloses that intramuscular immunization with a DNA vaccine encoding an epitope of cholesteryl ester transfer protein (CETP) consisting of 26 amino acids, which is displayed by Hepatitis B virus core (HBc) antigen protein, and containing CpG DNA inhibits arteriosclerosis in a rabbit arteriosclerosis model. This DNA vaccine is designed to permit insertion of CETP epitope between the amino acid residues 80-81 of the HBc antigen protein.

Non-patent document 6 discloses that the position of heterologous epitopes inserted in Hepatitis B virus core (HBc) antigen protein determines their immunogenicity. It discloses that insertion of an epitope between the amino acid residues 75-81 of the Hepatitis B virus core (HBc) antigen protein results in an increased antibody titer to the inserted epitope and decreased antibody titer to HBc.

Non-patent document 7 discloses that hybrid HBcAb-CS particles designed to permit insertion of malaria CS protein repeat epitope between the amino acid residues 75-81 of Hepatitis B virus core (HBc) antigen protein prevented malaria infection in mouse.

To potentiate the immune effect, it has been proposed to add an immunostimulatory sequence (ISS) as an adjuvant to a vaccine, or insert ISS into an expression vector of the active ingredient (non-patent document 8).

However, the effectiveness of the vaccine for lifestyle-related diseases such as hypertension and the like is not sufficiently satisfactory.

DOCUMENT LIST

Patent Documents patent document 1: JP-B-3228737
patent document 2: WO2003/031466
patent document 3: WO99/15655

Non-Patent Documents non-patent document 1: T. H. Do et al., Expert Opin. Biol. Ther., vol. 10, no. 7, pp. 1077-1087, 2010
non-patent document 2: D. C. Whitacre et al., Expert Rev. Vaccines, vol. 8, no. 11, pp. 1565-1573, 2009
non-patent document 3: B. E. Clarke et al., Nature, vol. 330, pp. 381-384, 1987
non-patent document 4: P. M. Ambuhl et al., Journal of Hypertension, vol. 25, no. 1, pp. 63-72, 2007 non-patent document 5: D. Mao et al., Vaccine, vol. 24, pp. 4942-4950, 2006 non-patent document 6: F. Schodel et al., Journal of Virology, vol. 66, no. 1, pp. 106-114, 1992 non-patent document 7: F. Schodel et al., The Journal of Experimental Medicine, vol. 180, pp. 1037-1046, 1994 non-patent document 8: J D Marshall et al., Journal of Leukocyte Biology, vol. 82, pp. 497-508, 2007

SUMMARY OF THE INVENTION

Problems to be Solved by the Invention

The present invention aims to provide a superior vaccine for lifestyle-related diseases such as hypertension, hyperlipidemia and the like.

Means of Solving the Problems

The present inventors have conducted intensive studies and found that an expression vector encoding an angiotensin II specific epitope inserted between the amino acid residues 80 and 81 of hepatitis B virus core antigen polypeptide can treat hypertension well. They have studied the administration mode of the expression vector in detail and succeeded in achieving unexpectedly good treatment results by subcutaneous administration with a needleless injector and the like. Furthermore, they have monitored antibody titer to angiotensin II induced by vaccine administration to find an extremely high antibody titer by only 3 times of administration. Based on these findings, they have further studied and completed the present invention.

That is, the present invention relates to the following.

[1] A therapeutic or improving agent for a lifestyle-related disease, comprising an expression vector encoding a chimeric Hepatitis B virus core antigen polypeptide inserted with an amino acid sequence comprising a specific epitope of a lifestyle-related disease-related factor, wherein the amino acid sequence comprising the specific epitope is inserted between the amino acid residues 80 and 81 of the hepatitis B virus core antigen polypeptide.

[2] The therapeutic or improving agent of [1], wherein the lifestyle-related disease is one kind selected from the group consisting of hypertension and hyperlipidemia.

[3] The therapeutic or improving agent of [1] or [2], wherein the lifestyle-related disease-related factor is angiotensin II (AngII) or cholesteryl ester transfer protein (CETP).

[4] The therapeutic or improving agent of [3], wherein the lifestyle-related disease-related factor is angiotensin II (AngII), and the amino acid sequence comprising the specific epitope is the amino acid sequence shown by SEQ ID NO: 16.

[5] A therapeutic or improving agent for hypertension, comprising an expression vector encoding a chimeric Hepatitis B virus core antigen polypeptide inserted with the amino acid sequence shown by SEQ ID NO: 16, wherein the amino acid sequence is inserted between the amino acid residues 80 and 81 of the hepatitis B virus core antigen polypeptide.

[6] The therapeutic or improving agent of [3], wherein the lifestyle-related disease-related factor is cholesteryl ester transfer protein (CETP), and the amino acid sequence comprising the specific epitope is the amino acid sequence shown by SEQ ID NO: 17.

[7] A therapeutic or improving agent for hyperlipidemia, comprising an expression vector encoding a chimeric Hepatitis B virus core antigen polypeptide inserted with the amino acid sequence shown by SEQ ID NO: 17, wherein the amino acid sequence is inserted between the amino acid residues 80 and 81 of the hepatitis B virus core antigen polypeptide.

[8] The therapeutic or improving agent of any one of [1]-[7], further comprising an immunostimulatory sequence (ISS) incorporated into the expression vector.

[9] The therapeutic or improving agent of [8], wherein the immunostimulatory sequence (ISS) consists of the nucleotide sequence shown by SEQ ID NO: 22.

[10] The therapeutic or improving agent of any one of [1]-[9], which is subcutaneously administered using a needleless injector.

[11] The therapeutic or improving agent of [10], wherein the needleless injector is a pressure injector.

[12] The therapeutic or improving agent of any one of [1]-[11], which is administered plural times.

[13] The therapeutic or improving agent of [12], wherein the administration number is 2 or 3.

[14] The therapeutic or improving agent of [13], wherein the administration number is 3.

[15] The therapeutic or improving agent of any one of [1]-[14], which is administered 3 times at 2-week intervals.

[16] An injection preparation for the treatment or improvement of a lifestyle-related disease, comprising an expression vector encoding a chimeric Hepatitis B virus core antigen polypeptide inserted with an amino acid sequence comprising a specific epitope of a lifestyle-related disease-related factor and a needleless injector, wherein the amino acid sequence comprising the specific epitope is inserted between the amino acid residues 80 and 81 of the hepatitis B virus core antigen polypeptide, and wherein the expression vector is enclosed in the needleless injector.

[17] An expression vector encoding a chimeric Hepatitis B virus core antigen polypeptide inserted with an amino acid sequence comprising a specific epitope of a lifestyle-related disease-related factor, which is for use in the treatment or improvement, of the lifestyle-related disease, wherein the amino acid sequence comprising the specific epitope is inserted between the amino acid residues 80 and 81 of the hepatitis B virus core antigen polypeptide.

[18] An expression vector encoding a chimeric Hepatitis B virus core antigen polypeptide inserted with the amino acid sequence shown by SEQ ID NO: 16, which is for use in the treatment or improvement of hypertension, wherein the amino acid sequence is inserted between the amino acid residues 80 and 81 of the hepatitis B virus core antigen polypeptide.

[19] An expression vector encoding a chimeric Hepatitis B virus core antigen polypeptide inserted with the amino acid sequence shown by SEQ ID NO: 17, which is for use in the treatment or improvement of hyperlipidemia, wherein the amino acid sequence is inserted between the amino acid residues 80 and 81 of the hepatitis B virus core antigen polypeptide.

[20] An injection preparation comprising an expression vector encoding a chimeric Hepatitis B virus core antigen polypeptide inserted with an amino acid sequence comprising a specific epitope of a lifestyle-related disease-related factor and a needleless injector, which is for use in the treatment or improvement of the lifestyle-related disease, wherein the amino acid sequence comprising the specific epitope is inserted between the amino acid residues 80 and 81 of the hepatitis B virus core antigen polypeptide, and wherein the expression vector is enclosed in the needleless injector.

[21] A method for the treatment or improvement of a lifestyle-related disease in a mammal, comprising administering an effective amount of an expression vector encoding a chimeric Hepatitis B virus core antigen polypeptide inserted with an amino acid sequence comprising a specific epitope of the lifestyle-related disease-related factor to the mammal, wherein the amino acid sequence comprising the specific epitope is inserted between the amino acid residues 80 and 81 of the hepatitis B virus core antigen polypeptide.

[22] A method for the treatment or improvement of hypertension in a mammal, comprising administering an effective amount of an expression vector encoding a chimeric Hepatitis B virus core antigen polypeptide inserted with the amino acid sequence shown by SEQ ID NO: 16 to the mammal, wherein the amino acid sequence is inserted between the amino acid residues 80 and 81 of the hepatitis B virus core antigen polypeptide.

[23] A method for the treatment or improvement of hyperlipidemia in a mammal, comprising administering an effective amount of an expression vector encoding a chimeric Hepatitis B virus core antigen polypeptide inserted with the amino acid sequence shown by SEQ ID NO: 17 to the mammal, wherein the amino acid sequence is inserted between the amino acid residues 80 and 81 of the hepatitis B virus core antigen polypeptide.

[24] A method for the treatment or improvement of a lifestyle-related disease, comprising injecting an effective amount of an expression vector encoding a chimeric Hepatitis B virus core antigen polypeptide inserted with an amino acid sequence comprising a specific epitope of the lifestyle-related disease-related factor to a mammal with a needleless injector, wherein the amino acid sequence comprising the specific epitope is inserted between the amino acid residues 80 and 81 of the hepatitis B virus core antigen polypeptide.

[25] Use of an expression vector encoding a chimeric Hepatitis B virus core antigen polypeptide inserted with an amino acid sequence comprising a specific epitope of a lifestyle-related disease-related factor for producing a therapeutic or improving agent for a lifestyle-related disease, wherein the amino acid sequence comprising the specific epitope is inserted between the amino acid residues 80 and 81 of the hepatitis B virus core to antigen polypeptide.

[26] Use of an expression vector encoding a chimeric Hepatitis B virus core antigen polypeptide inserted with the amino acid sequence shown by SEQ ID NO: 16 for producing a therapeutic or improving agent for hypertension, wherein the amino acid sequence is inserted between the amino acid residues 80 and 81 of the hepatitis B virus core antigen polypeptide.

[27] Use of an expression vector encoding a chimeric Hepatitis B virus core antigen polypeptide inserted with the amino acid sequence shown by SEQ ID NO: 17 for producing a therapeutic or improving agent for hyperlipidemia, wherein the amino acid sequence is inserted between the amino acid residues 80 and 81 of the hepatitis B virus core antigen polypeptide.

[28] Use of an expression vector encoding a chimeric Hepatitis B virus core antigen polypeptide inserted with an amino acid sequence comprising a specific epitope of a lifestyle-related disease-related factor and a needleless injector, for producing a therapeutic or improving agent for the lifestyle-related disease, wherein the amino acid sequence comprising the specific epitope is inserted between the amino acid residues 80 and 81 of the hepatitis B virus core antigen polypeptide.

Effect of the Invention

A superior vaccine for the treatment or prophylaxis of a lifestyle-related disease such as hypertension, hyperlipidemia and the like is provided.

DESCRIPTION OF EMBODIMENTS

Figure 1:
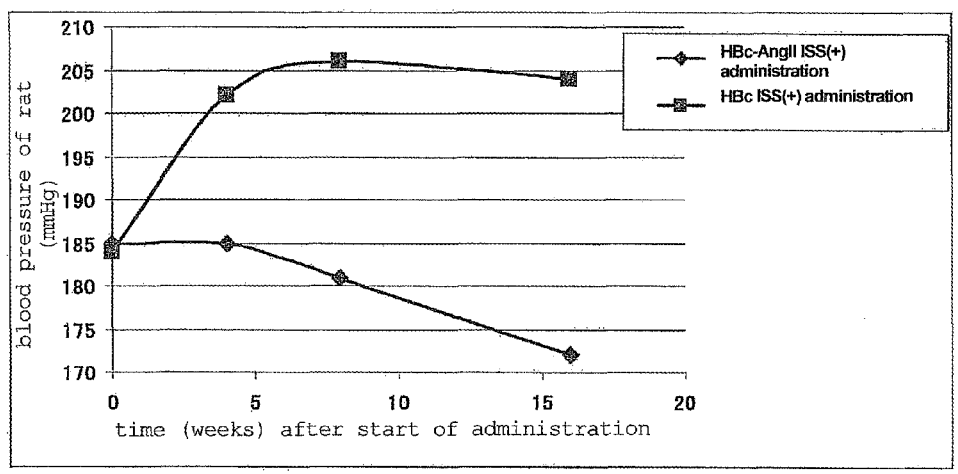
FIG. 1 shows the effect of HBc-AngII ISS(+) administration on hypertension, wherein the vertical axis shows the rat blood pressure (mmHg) and the horizontal axis shows the time (weeks) after the start of the administration.

The present invention provides a therapeutic or improving agent for a lifestyle-related disease, comprising an expression vector encoding a chimeric Hepatitis B virus core antigen polypeptide inserted with an amino acid sequence comprising a specific epitope of a lifestyle-related disease-related factor, wherein the amino acid sequence comprising the epitope is inserted between the amino acid residues 80 and 81 of the hepatitis B virus core antigen polypeptide.

In the present specification, the lifestyle-related disease is a generic term of the diseases caused by lifestyle such as dietary habits, exercise habits, rest, smoking, alcohol drinking and the like. Examples of the lifestyle-related disease include hypertension, hyperlipidemia, diabetes, arteriosclerosis, ischemic disease (myocardial infarction, cerebral apoplexy etc.), obesity and the like. The lifestyle-related disease is preferably hypertension or hyperlipidemia, particularly preferably hypertension.

In the present specification, the lifestyle-related disease-related factor means a polypeptide that contributes to the aggravation of lifestyle-related diseases. The therapeutic or improving agent of the present invention treats or improves the lifestyle-related disease by inducing production of an antibody to a lifestyle-related disease-related factor and neutralizing the lifestyle-related disease-related factor by the antibody. In consideration of this mechanism, therefore, the lifestyle-related disease-related factor is preferably a factor secreted extracellularly or a factor expressed on the cell surface, so that it will be recognized by an antibody induced in the body of the patient.

Examples of the hypertension-related factor include polypeptides that contribute to an increase in the blood pressure such as angiotensin II, angiotensin I, ACE, rennin, AT-1 receptor and the like. The hypertension-related factor is preferably angiotensin II.

Examples of the hyperlipidemia-related factor include polypeptides that contribute to an increase in the lipid (particularly, cholesterol or triglyceride) concentration in the blood such as cholesteryl ester transfer protein (CETP) and the like.

In the present invention, use of a lifestyle-related disease-related factor derived from a mammal of the same species as the mammal to be the application target of the therapeutic or improving agent of the present invention is intended. The application target of the therapeutic or improving agent of the present invention is a mammal. Examples of the mammal include rodents such as mouse, rat, hamster, guinea pig and the like, lagomorphas such as rabbit and the like, ungulates such as swine, bovine, goat, horse, sheep and the like, carnivore such as dog, cat and the like, primates such as human, monkey, *Macaca mulatta*, *Macaca fascicularis*, marmoset, orangutan, chimpanzee and the like, and the like. The mammal is preferably a rodent (mouse etc.) or a primate (human etc.). Therefore, for example, when the therapeutic or improving agent of the present invention is applied to human, use of a lifestyle-related disease-related factor derived from a human is intended. When the therapeutic or improving agent of the present invention is applied to mouse, use of a lifestyle-related disease-related factor derived from a mouse is intended.

In the present specification, regarding the particular factor X (polypeptide or polynucleotide), "factor X derived from organism Y" or "organism Y factor X" means that the amino acid sequence or nucleic acid sequence of factor X has the same or substantially the same amino acid sequence or nucleic acid sequence as the amino acid sequence or nucleic acid sequence of factor X naturally expressed in organism Y. Being "substantially the same" means that the amino acid sequence or nucleic acid sequence of interest has not less than 70% (preferably not less than 80%, more preferably not less than 90%, still more preferably not less than 95%, most preferably not less than 99%) identity with the amino acid sequence or nucleic acid sequence of factor X naturally expressed in organism Y, and the function of factor X is maintained.

In the present specification, "epitope" refers to a basic element or minimum unit for recognition by each antibody or T cell receptor, which is a particular domain, region or molecular structure the aforementioned antibody or T cell receptor binds to.

The epitope of the lifestyle-related disease-related factor is preferably specific to the lifestyle-related disease-related factor. Being "specific" means that a gene product other than the lifestyle-related disease-related factor, which is naturally expressed in the mammal from which the lifestyle-related disease-related factor is derived, does not contain the epitope.

As the epitope of the lifestyle-related disease-related factor, one at a position where the activity of the lifestyle-related disease-related factor is inhibited when an antibody that recognizes the epitope binds to the epitope, is preferably selected. Such epitope can be in a functional site, for example, ligand binding site, receptor binding site, substrate binding site, coenzyme binding site, divalent ion binding site, channel moiety, site recognized by a specific enzyme and the like. Those of ordinary skill in the art can appropriately select the epitope based on the steric structure and the like of the lifestyle-related disease-related factor.

The length of the amino acid sequence of the epitope is generally 5-30 amino acids, preferably 6-25 amino acids. When the amino acid sequence is too short, the antigenicity of the epitope may be lost. When the amino acid sequence is too long, chimeric hepatitis B virus core antigen polypeptide does not easily form core particles due to self-assembly, as a result of which an antibody that specifically recognizes the epitope may not be produced, and a superior treatment or improvement effect on a lifestyle-related disease may not be obtained.

Specific examples of a preferable epitope of a lifestyle-related disease-related factor include the following.
(angiotensin II) (WO2003/031466 and Journal of Hypertension, vol. 25, no. 1, pp. 63-72, 2007)

| a) | CGGDRVYIHPF | (SEQ ID NO: 4) |
| b) | CGGDRVYIHPFHL | (SEQ ID NO: 5) |
| c) | DRVYIHPFHLGGC | (SEQ ID NO: 6) |
| d) | CDRVYIHPFHL | (SEQ ID NO: 7) |
| e) | CHPFHL | (SEQ ID NO: 8) |
| f) | CGPFHL | (SEQ ID NO: 9) |
| g) | CYIHPF | (SEQ ID NO: 10) |
| h) | CGIHPF | (SEQ ID NO: 11) |
| i) | CGGHPF | (SEQ ID NO: 12) |
| j) | CRVYIGGC | (SEQ ID NO: 13) |
| k) | DRVYGGC | (SEQ ID NO: 14) |
| l) | DRVGGC | (SEQ ID NO: 15) |
| m) | DRVYIHPF | (SEQ ID NO: 16) |

The epitopes a)-l) are particularly useful for the treatment or improvement of lifestyle-related diseases (preferably hypertension) in human and mouse. The epitope sequence m) is useful for the treatment or improvement of lifestyle-related diseases (preferably hypertension) in human and rat.

The preferable epitope of angiotensin II is preferably DRVYIHPF (SEQ ID NO: 16). When the epitope is used, an antibody having higher specificity to angiotensin II than angiotensin I is induced.
(cholesteryl ester transfer protein (CETP)) (Vaccine, vol. 24, pp. 4942-4950, 2006)

| a) | RDGFLLLQMDFGFPEHLLVDFLQSL | (SEQ ID NO: 17) |

The epitope a) is particularly useful for the treatment or improvement of lifestyle-related diseases (preferably hyperlipidemia) in human, mouse and rabbit.

Hepatitis B virus core antigen polypeptide used in the present invention is
(1) a polypeptide containing the amino acid sequence shown by SEQ ID NO: 2, or
(2) a polypeptide containing an amino acid sequence having not less than 90% (preferably not less than 95%, more preferably not less than 97%, still more preferably not less than 99%) identity with the amino acid sequence shown by SEQ ID NO: 2, and having an activity to form core particles due to self-assembly.

Self-assembly refers to a phenomenon wherein molecules dissolved in a solution associate to form an assembly. Core particle refers to a rigid structure having a specific repetitive constitution. In the present specification, the core particle may be a product of synthesis steps or a product of biological steps.

As the polypeptide of the embodiment of (2), a polypeptide containing the amino acid sequence shown by SEQ ID NO: 3 disclosed in WO2003/031466 can be mentioned. A polypeptide containing the amino acid sequence shown by SEQ ID NO: 3 except that one or plural cysteine residues of the positions 48, 61, 107 and 185 are deleted or substituted by other amino acid residue (e.g., serine residue) is also preferable as the polypeptide of the embodiment of (2). As recognized by those of ordinary skill in the art, in a polypeptide having an amino acid sequence different from that of SEQ ID NO: 3, cysteine residues at similar positions can be deleted or substituted by other amino acid residues, and polypeptides obtained by such deletion and substitution are also encompassed in the polypeptide of the embodiment of (2).

The polypeptide of the embodiment of (2) also encompasses a variant polypeptide wherein the isoleucine residue at the position corresponding to the position 97 of SEQ ID NO: 3 is substituted by leucine residue or phenylalanine residue (Yuan et al., J. Virol. vol. 73, pages 10122-10128 (1999)). In addition, amino acid sequences of many HBcAg variants and several kinds of hepatitis B core antigen precursor variants are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X8529, X85307, X65257, X85311, X85301, X85314, X85287, X85272, X85319, AB010289, X85285, AB010289, AF121242, M90520, P03153, AF110999 and M95589 (each of the disclosures is incorporated in the present specification by reference), and polypeptides containing amino acid sequences of these variants are also encompassed in the polypeptide of the embodiment of (2). The above-mentioned variants have amino acid sequences different at many positions including amino acid residues corresponding to the amino acid residues present at the positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO: 3.

Furthermore, polypeptides containing the amino acid sequences of the HBcAg variants described in WO01/98333, WO01/77158 and WO02/14478, all of which are incorporated in the present specification by reference are also encompassed in the polypeptide of the embodiment of (2).

In the present specification, unless particularly indicated, the positions of amino acid residues in the amino acid sequence of hepatitis B virus core antigen polypeptide are specified with the amino acid sequence shown by SEQ ID NO: 2 as the standard. When a polypeptide does not contain the amino acid sequence shown by SEQ ID NO: 2, the amino acid sequence of the polypeptide is aligned with the amino acid sequence shown by SEQ ID NO: 2, and the position of the corresponding amino acid residue is adopted.

The hepatitis B virus core antigen polypeptide used in the present invention is preferably a polypeptide containing the amino acid sequence shown by SEQ ID NO: 2.

In the chimeric hepatitis B virus core antigen polypeptide to be used in the present invention, an amino acid sequence comprising an epitope of the above-mentioned a lifestyle-related disease-related factor is inserted between the amino acid residues 80 and 81 of the hepatitis B virus core antigen polypeptide. That is, the chimeric hepatitis B virus core antigen polypeptide to be used in the present invention contains the following elements (a)-(c):

(a) N-terminus part polypeptide residues of hepatitis B virus core antigen polypeptide (consisting of the continuous partial amino acid sequence of hepatitis B virus core antigen polypeptide from N-terminus to the amino acid residue 80),
(b) an amino acid sequence consisting of an epitope of a lifestyle-related disease-related factor, and
(c) C-terminus partial polypeptide residues of hepatitis B virus core antigen polypeptide (consisting of the continuous partial amino acid sequence of hepatitis B virus core antigen polypeptide from the amino acid residue 81 to C-terminus) in the order of (a), (b), (c) from the N terminal side.

The chimeric hepatitis B virus core antigen polypeptide to be used in the present invention having the above-mentioned constitution forms core particles due to self-assembly, and an epitope of a lifestyle-related disease-related factor is presented on the outside of the particles.

Element (a) and Element (b) may be directly connected by a covalent bond or via a spacer sequence. The element (a) and the element (b) are preferably connected via a spacer sequence so that an epitope of a lifestyle-related disease-related factor will be stably presented on the outside of the particles formed by self-assembly of chimeric hepatitis B virus core antigen polypeptides, while maintaining its structure. The spacer sequence means an amino acid sequence containing one or more amino acid residues inserted between two adjacent elements contained in the chimeric Hepatitis B virus core antigen polypeptide. While the length of the spacer sequence is not limited as long as chimeric hepatitis B virus core antigen polypeptide forms core particles due to self-assembly and an epitope of a lifestyle-related disease-related factor is presented on the outside of the particles, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms core particles due to self-assembly and an epitope of a lifestyle-related disease-related factor is presented on the outside of the particles. Examples of a preferable spacer sequence include, but are not limited to, IT, GAT, CGG and the like.

The element (b) and element (c) may be directly linked via a covalent bond, or via a spacer sequence. The element (b) and element (c) are preferably linked via a spacer sequence to the outside of the core particles formed by self-assembly of chimeric Hepatitis B virus core antigen polypeptide, so that an epitope of a lifestyle-related disease-related factor can be presented stably while maintaining the structure thereof. While the length of the spacer sequence is not limited as long as chimeric hepatitis B virus core antigen polypeptide forms core particles due to self-assembly and an epitope of a lifestyle-related disease-related factor is presented on the outside of the particles, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms core particles due to self-assembly and an epitope of a lifestyle-related disease-related factor is presented on the outside of the particles. Examples of the preferable spacer sequence include, but are not limited to, IT, GAT, CGG and the like.

In a preferable embodiment, element (a) and element (b) are linked via a spacer sequence IT, and element (b) and element (c) are linked via a spacer sequence GAT.

The expression vector used in the present invention is a recombinant vector incorporating a polynucleotide encoding the above-mentioned chimeric hepatitis B virus core antigen polypeptide. When the expression vector is administered to a target mammal, the expression vector is intracellularly incorporated into the target mammal, and the cell expresses the above-mentioned chimeric hepatitis B virus core antigen polypeptide. Examples of the expression vector inserted with polynucleotide encoding chimeric hepatitis B virus core antigen polypeptide include plasmid, virus, phage, cosmid and other vectors conventionally used in the art. Examples of the plasmid vector include, but are not limited to, pCAGGS (Gene 108: 193-199 (1991)), pCR-X8 (Vaccine 24: 4942-4950 (2006)), pcDNA3.1 (trade name, Invitrogen), pZeoSV (trade name, Invitrogen), pBK-CMV (trade name, Stratagene) and the like. The virus vector is a DNA virus or an RNA virus. Examples of the virus vector include, but are not limited to, detoxicated retrovirus, adenovirus, adeno-associated virus, herpes virus, vaccinia virus, poxvirus, polio virus, Sindbis virus, Hemagglutinating Virus of Japan (HVJ), SV40, human immunodeficient virus (HIV) and the like. Furthermore, Hemagglutinating Virus of Japan envelope (HVJ-E) and the like can also be utilized.

In the above-mentioned expression vector, polynucleotide (preferably DNA) encoding chimeric hepatitis B virus core antigen polypeptide is operably connected to a promoter capable of exhibiting a promoter activity in the cell of a mammal (preferably human) to be the administration subject.

The promoter to be used is not particularly limited as long as it can function in the cell of a mammal (preferably human) to be the administration subject. Examples of the promoter include pol I promoter, pol II promoter, pol III promoter and the like. Specifically, virus promoters such as SV40-derived initial promoter, cytomegalovirus LTR and the like, mammal constituting protein gene promoters such as β-actin gene promoter and the like, RNA promoters such as tRNA promoter and the like, and the like are used.

The above-mentioned expression vector preferably contains a transcription termination signal, i.e., terminator region, at the downstream of the polynucleotide encoding chimeric hepatitis B virus core antigen polypeptide. It can further contain a selection marker gene for the selection of a transformed cell (gene conferring resistance to medicaments such as tetracycline, ampicillin, kanamycin and the like, gene complementing auxotrophic mutation etc.).

In one embodiment, the above-mentioned expression vector may contain an immune stimulatory sequence (ISS) (also referred to as CpG) to potentiate the immune effect. The immune stimulatory sequence is a DNA containing a non-methylated CpG motif of bacterium, and is known to function as a ligand of a particular receptor (Toll-like receptor 9) (see Biochim. Biophys. Acta 1489, 107-116 (1999) and Curr. Opin. Microbiol. 6, 472-477 (2003) for the detail). Preferable examples of the immune stimulatory sequence include the following.

```
CpG-B1018 22 bp
5'-tga ctg tga acg ttc gag atg     (SEQ ID NO: 18)
a-3'

CpG-A D19 20 bp (D type)
5'-ggt gca tcg atg cag ggg gg-3'   (SEQ ID NO: 19)

CpG-CC274 21 bp
5'-tcg tcg aac gtt cga gat gat-3'  (SEQ ID NO: 20)

CpG-CC695 25 bp
5'-tcg aac gtt cga acg ttc gaa cgt  (SEQ ID NO: 21)
t-3'
```

Alternatively, 2, 3 or 4 from these ISSs may be connected and used. Preferable examples of the connected ISS sequence include the following.
5'-ggt gca tcg atg cag ggg gg tga ctg tga acg ttc gag atg a tcg tcg aac gtt cgagat gat tcg aac gtt cga acg ttc gaa cgt t-3' (SEQ ID NO: 22)

Those of ordinary skill in the art can construct the aforementioned expression vector according to well-known genetic engineering techniques described in, for example, "edit. Sambrook et al., Molecular Cloning A Laboratory Manual Cold Spring Harbor Laboratory (1989) N.Y.", "edit. Ausubel et al., Current Protocols in Molecular Biology (1987) John Wiley & Sons" and the like.

The therapeutic or improving agent of the present invention can be provided as a pharmaceutical composition containing, in addition to a therapeutically effective amount of the above-mentioned expression vector, any carrier, for example, a pharmaceutically acceptable carrier.

Examples of the pharmaceutically acceptable carrier include, though not limited thereto, excipients such as sucrose, starch, mannit, sorbit, lactose, glucose, cellulose, talc, calcium phosphate, calcium carbonate and the like, binders such as cellulose, methylcellulose, hydroxypropylcellulose, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyrrhizin.ammonium salt, glycine, orange power and the like, preservatives such as sodium benzoate, sodium bisulfite, methylparaben, propylparaben and the like, stabilizers such as citric acid, sodium citrate, acetic acid and the like, suspending agent such as methylcellulose, polyvinylpyrrolidone, aluminum stearate and the like, dispersing agents such as surfactant and the like, diluents such as water, saline and the like, base waxes such as cacao butter, polyethylene glycol, white kerosine and the like, and the like.

The therapeutic or improving agent of the present invention may further contain an adjuvant to potentiate its effect. Examples of the adjuvant include aluminum hydroxide, complete Freund's adjuvant, incomplete Freund's adjuvant, pertussis adjuvant, poly(I:C), CpG-DNA and the like.

To promote intracellular introduction of an expression vector, the therapeutic or improving agent of the present invention may further contain a reagent for nucleic acid introduction. As the reagent for nucleic acid introduction, cationic lipids such as lipofectin (trade name, Invitrogen), lipofectamine (trade name, Invitrogen), transfectam (trade name, Promega), DOTAP (trade name, Roche Applied Science), dioctadecylamidoglycyl spermine (DOGS), L-dioleoyl phosphatidyl-ethanolamine (DOPE), dimethyldioctadecyl-ammonium bromide (DDAB), N,N-di-n-hexadecyl-N,N-dihydroxyethylammonium bromide (DHDEAB), N-n-hexadecyl-N,N-dihydroxyethylammonium bromide (HDEAB), polybrene, poly(ethyleneimine) (PEI) and the like can be used. In addition, an expression vector may be included in any known liposome constituted of a lipid bilayer such as electrostatic liposome. Such liposome may be fused with a virus such as inactivated Hemagglutinating Virus of Japan (HVJ). HVJ-liposome has a very high fusion activity with a cellular membrane, as compared to general liposomes. When retrovirus is used as an expression vector, RetroNectin, fibronectin, polybrene and the like can be used as transfection reagents.

While the content of the above-mentioned expression vector in the pharmaceutical composition is not particularly limited and appropriately selected from a wide range, it is generally about 0.00001 to 100 wt % of the whole pharmaceutical composition.

By introducing the above-mentioned expression vector into an application target, mammalian tissue (or cell), the therapeutic or improving agent of the present invention induces in vivo expression of the above-mentioned chimeric Hepatitis B virus core antigen polypeptide, induces production of an antibody to the epitope of the lifestyle-related disease-related factor contained in the chimeric Hepatitis B virus core antigen polypeptide, and treats or improves the lifestyle-related disease of the mammal by neutralization of the activity of the lifestyle-related disease-related factor by the induced antibody. Various methods for introducing nucleic acids such as expression vector and the like into the body are known (T. Friedman, Science 244: 1275-1281 (1989)), and any introduction method can be adopted as long as it can induce in vivo expression of the above-mentioned chimeric Hepatitis B virus core antigen polypeptide, induce production of an antibody to the epitope of the lifestyle-related disease-related factor contained in the chimeric Hepatitis B virus core antigen polypeptide, and treat or improve the lifestyle-related disease.

Examples of the method for introducing an expression vector into a mammalian tissue (or cell) in vivo include, but are not limited to, inner liposome method, electrostatic liposome method, HVJ-liposome method, HVJ-AVE liposome method, receptor-mediated transgene, particle gun method, naked DNA method, introduction method by positive electric charge polymer and the like.

Alternatively, cells such as blood cells, bone marrow cells and the like may be isolated from the application target mammal, the above-mentioned expression vector may be introduced into the cells ex vivo, after which the obtained cells containing the above-mentioned expression vector may be returned to the application target mammal.

Examples of the method for introducing an expression vector into a mammalian cell ex vivo include, but are not limited to, lipofection method, calcium phosphate coprecipitation method, DEAE-dextran method, direct DNA introduction method using glass'microcapillary and the like.

The therapeutic or improving agent of the present invention may be administered by any method as long as in the administration subject mammal, the agent induces in vivo expression of the above-mentioned chimeric hepatitis B virus core antigen polypeptide, induces production of an antibody to the epitope of the lifestyle-related disease-related factor contained in the chimeric hepatitis B virus core antigen polypeptide, and treats or improves the lifestyle-related disease. Preferably, the therapeutic or improving agent of the present invention is parenterally administered in an amount sufficient to induce production of an antibody to the epitope of the lifestyle-related disease-related factor contained in the chimeric hepatitis B virus core antigen polypeptide, and treat or improve the lifestyle-related disease. For example, injection via intravenous, intraperitoneal, subcutaneous, intradermal, intraadipose tissue, intramammary gland tissue, or intramuscular pathway; gas induced particle bombarding method (by electron gun and the like); a method in the form of collunarium and the like via a mucosal pathway, and the like are recited as examples of the administration methods. In one embodiment, the therapeutic or improving agent of the present invention is injected subcutaneously or intramuscularly, preferably subcutaneously.

In one embodiment, the therapeutic or improving agent of the present invention is subcutaneously administered by a needleless injector. The needleless injector is preferably a pressure injector. Examples of the needleless injector include, but are not limited to, ShimaJET (trade name, SHIMADZU CORPORATION), Twinject EZII (trade name, Japan chemical research), Syrijet (trade name, Keystone), ZENEO (trade name, Crossject) and the like. In this case, the therapeutic or improving agent of the present invention can be provided as an injection preparation containing the above-mentioned expression vector and needleless injector, wherein the expression vector is enclosed in the needleless injector.

In one embodiment, the therapeutic or improving agent of the present invention is administered subcutaneously, intradermally or intramuscularly with a gene gun. In this case, the above-mentioned expression vector may be applied onto the carrier particles such as colloidal gold particles and the like to be introduced into the body and used for administration. A technique for coating carrier particles with polynucleotide is known (see, for example, WO93/17706). Finally, the expression vector can be prepared in an aqueous solution such as physiological saline and the like suitable for administration to the body.

To induce good immune responses, the therapeutic or improving agent of the present invention is preferably administered plural times at given intervals. While the frequency can be appropriately determined by monitoring the to level of immune response, it is generally 2-10 times, preferably 2-6 times, more preferably 2-4 times, most preferably 3 times.

The administration frequency is generally once per 3 days-3 months, preferably once per 1-4 weeks, more preferably once per 1.5-3 weeks, most preferably once per 2 weeks.

In one embodiment, the therapeutic or improving agent of the present invention is administered to a target mammal 3 times at 2 weeks intervals.

While the dose of the therapeutic or improving agent of the present invention depends on the immunogenicity of the epitope of the lifestyle-related disease-related factor contained in the chimeric hepatitis B virus core antigen polypeptide encoded by the active ingredient expression vector in an administration subject mammal, those of ordinary skill in the art can determine the dose necessary for a good immune response by administering a given amount of an expression vector to an administration subject mammal, measuring the antibody titer specific to the epitope by a detection method such as ELISA and the like, and observing the immune response. Those of ordinary skill in the art appreciate that the immunogenicity of the therapeutic or improving agent of the present invention also depends on the strength of the regulatory sequence such as promoter used for the expression vector as an active ingredient. Moreover, those of ordinary skill in the art can also control the dose of the therapeutic or improving agent of the present invention with ease depending on the kind of the expression vector to be used.

All references cited herein, including patents and patent applications, are hereby incorporated in full by reference, to the extent that they have been disclosed herein.

The present invention is explained in more detail in the following by referring to Examples, which do not limit the present invention in any way.

EXAMPLES

Example 1

1. Method 1-1. Preparation of Construct Expressing HBc-AngII
1-1-1. Preparation of HBc-AngII, HBc Sequence and TA Cloning Plasmid pPLc3 (Accession number LMBP 2470) was purchased from BCCM/LMBP Plasmid Collection. The following primer was designed and synthesized.

HBcF
(SEQ ID NO: 23)
5'-gcc atg gat atc gat cct tat aaa gaa ttc gga gc-3'

HBcR
(SEQ ID NO: 24)
5'-ggc ctc tca cta aca ttg aga ttc ccg aga ttg aga-3'

H2
(SEQ ID NO: 25)
5'-ggg gtg gat gta tac gcg gtc agt gat agc tgg atc ttc caa gtt aac-3'

H3-II
(SEQ ID NO: 26)
5'-c cgc gta tac atc cac ccc ttt ggt gct act agc agg gac ctg gta gtc-3'

The respective primer sequences correspond to the following positions of the nucleotide sequence (SEQ ID NO: 1) encoding the Hepatitis B virus core (HBc) antigen protein.
HBc F: the 1st-33rd nucleotides.
HBc R: the 527th-556th nucleotides.
H2: nucleotide encoding 2 amino acids (IT) of the spacer and a part of AngII sequence are linked to the 221st-241st nucleotides.
H3-II: a part of AngII sequence and 3 amino acids (GAT) of the spacer are linked to the 242nd-259th nucleotides.

Firstly, using a template (plasmid pPLc3) and a primer set (HBc F and H2), the first DNA fragment containing N-terminus of HBc, a spacer and a part of AngII was amplified by PCR. Furthermore, using a template (plasmid pPLc3) and a primer set (H3-II and HBc R), the second DNA fragment containing a part of AngII, a spacer and C-terminus of HBc was amplified by PCR. The both amplification products share partly overlapped AngII sequences. Utilizing annealing of the overlapped portion, the first DNA fragment and the second DNA fragment were linked by the third PCR (primer set; HBc F and HBc R) to give an amplification product (HBc-AngII). That is, a spacer and a nucleotide sequence encoding a polypeptide containing a partial sequence of AngII were inserted between the 241st base and the 242nd base of a nucleotide sequence (SEQ ID NO: 1) encoding a Hepatitis B virus core (HBc) antigen protein. The amino acid sequence encoded by the inserted nucleotide sequence was IT-DRVYIHPF-GAT (SEQ ID NO: 27, 13 amino acids). TA cloning of HBc-AngII into pcDNA 3.1/V5-His TOPO TA Expression Kit (Invitrogen) was performed to give the HBc-AngII ISS(−) vector. Similarly, PCR was performed using a template (plasmid pPLc3) and a primer set (HBcF and HBcR) to prepare a DNA fragment encoding a full-length polypeptide of HBc, and TA cloning thereof into the pcDNA 3.1/V5-His TOPO vector was performed to give the HBc ISS(−) vector.

1-1-2. Preparation of HBc-AngII ISS(+), HBc ISS(+) Vector (Preparation of ISS Sequence and Insertion into Vector)

The following templates (CpG (A+B+C+C)-F and CpG (A+B+C+C)-R) and primers (DraIII-F and DraIII-R) were designed and synthesized.

```
CpG (A + B + C + C)-F
                                    (SEQ ID NO: 28)
5'-ggt gca tcg atg cag ggg gg tga ctg tga acg ttc gag atg a tcg tcg aac gtt cga gat gat tcg aac gtt cga acg ttc gaa cgt t-3'

CpG (A + B + C + C)-R
                                    (SEQ ID NO: 29)
5'-a acg ttc gaa cgt tcg aac gtt cga -atc atc tcg aac gtt cga cga -t cat ctc gaa cgt tca cag tca -cc ccc ctg cat cga tgc acc-3'

DraIII-F
                                    (SEQ ID NO: 30)
5'-ttt-cacgtagtg- ggt gca tcg atg cag g-3'

DraIII-R
                                    (SEQ ID NO: 31)
5'-ggt-cactacgtg- a acg ttc gaa cgt tcg-3'
```

Using CpG (A+B+C+C)-F and CpG (A+B+C+C)-R as templates and a primer set of DraIII-F and DraIII-R, PCR was performed to give a DNA fragment containing ISS sequence having DraIII site at both ends (DraIII-ISS). Then, DraIII-ISS and vectors HBc-AngII ISS(−) and HBc ISS(−) were digested with DraIII. The vectors were treated with alkaline phosphatase, and ligated with the enzymatic digestion product of DraIII-ISS to insert ISS into the DraIII site (1621) of the vectors.

1-2. Animal Experiment

Each vector was administered 3 times (100 μg/μl×2 sites/time) to the back skin of 10-week-old hypertension rat (SHR) every 2 weeks using ShimaJET (trade name, SHIMADZU CORPORATION).

HBc-AngII ISS(+) group: 12 rats

HBc ISS(+) group: 7 rats

Administered at 0 week, 2 weeks, 4 weeks, and the blood pressure measurement, serum collection and antibody titer measurement were performed at 0 week, 4 weeks, 8 weeks, 16 weeks from the start of the administration.

1-2-1(a). Tail-Cuff Method (1)

(Measurement Device of Tail-Cuff Method)

maker: Softron product name BP-98A (rat-mouse noninvasive automatic blood pressure measurement apparatus)

1-2-1(a). Tail-Cuff Method (2)

(Reference Document)

Evaluation of New Tail-cuff Method for Blood Pressure Measurement in Rats with Special Reference to the Effect of Ambient Temperature EXPERIMENTAL ANIMALS Vol. 40 No. 3: 331-336 (1991)

Antihypertensive Effect of Sesamin. I. Protection against Deoxycorticosterone Acetate-Salt-Induced Hypertension and Cardiovascular Hypertrophy BIOLOGICAL & PHARMACEUTICAL BULLETIN Vol. 18 1016-1019 (1995)
Establishment of an adrenocortical carcinoma xenograft with normotensive hyperaldosteronism in vivo
APMIS 106:1056-1060 (1998)
Endotherin-1 enhances Pressor Responses to Norepinephrine Involvement of Endothelin-B Receptor
JOURNAL OF CARDIOVASCULAR PHARMACOLOGY Vol. 13 119-121 (1998)
Effect of dopamine receptor antagonists on the calcium-dependent central function that reduces blood pressure in spontaneously hypertensive rats.
ELSEVIER NEUROSCIENCE LETTERS Vol. 269 133-136 (1999)
Leprosy in Hypertensive Nude Rats (SHR/NCrj-rnu)
INTERNATIONAL JOURNAL OF LEPROSY Vol. 67 No. 4 435-443 (1999)
Potentiation by endothelin-1 of vasoconstrictor response in stroke-prone spontaneously hypertensive rats.
EUROPEAN JOURNAL OF PHARMACOLOGY Vol. 415 45-49 (2001)

1-2-1(b). Blood Pressure Measurement by Tail-Cuff Method
(Method)
The blood pressure measurement was performed by a tail-cuff method. The measurement was performed 5-15 times per animal, and an average thereof was used.
(Results)
The HBc ISS(+) group (control) showed an increase in the blood pressure of SHR rats. On the other hand, HBc-AngII ISS(+) group showed a obvious decrease in the blood pressure (FIG. 1).

1-2-2(a). ELISA Method
(Reagent and Measurement Device)
Angiotensin II-BSA conjugate, Angiotensin I-BSA conjugate: prepared using DSS (Disuccinimidyl suberate) as a spacer
Angiotensinogen (Human): sigma A2562
Nunc Maxisorp (Cat. 442404)
3% skim milk (PBS dilution)
PBS-T (0.05% Tween)
$2^{nd}$ antibody: HRP-conjugated anti-mouse IgG secondary antibody (GE, NA931V), HRP-conjugated anti-rat IgG secondary antibody (GE, NA935V)
TMB solution: sigma T0440
stop solution: $0.5N\ H_2SO_4$
microplate reader (InterMed, ImmunoMini NJ-2300)

Figure 2:
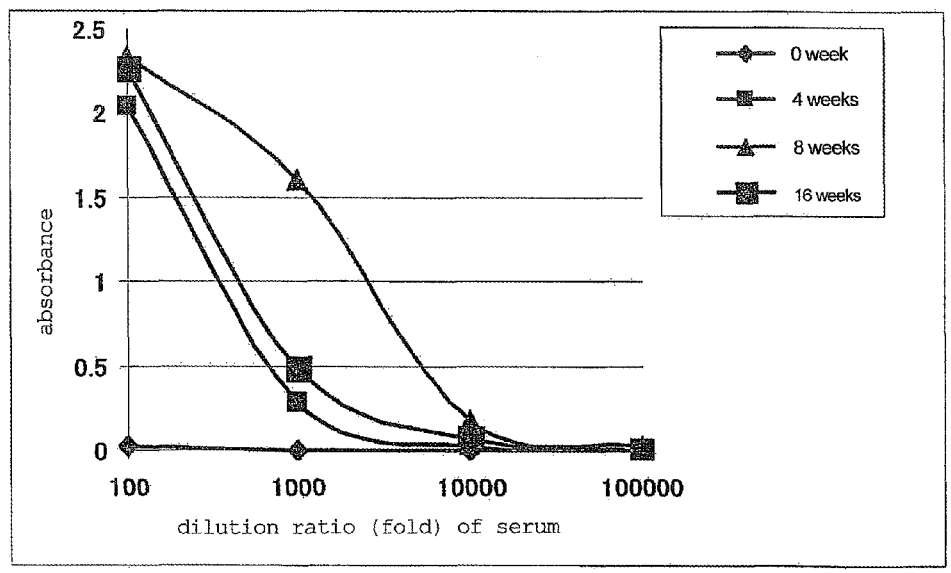
FIG. 2 shows time-course changes of the antibody titer to AngII induced by HBc-AngII ISS(+) administration, wherein the vertical axis shows absorbance and the horizontal axis shows the dilution ratio of the serum.
Figure 3:
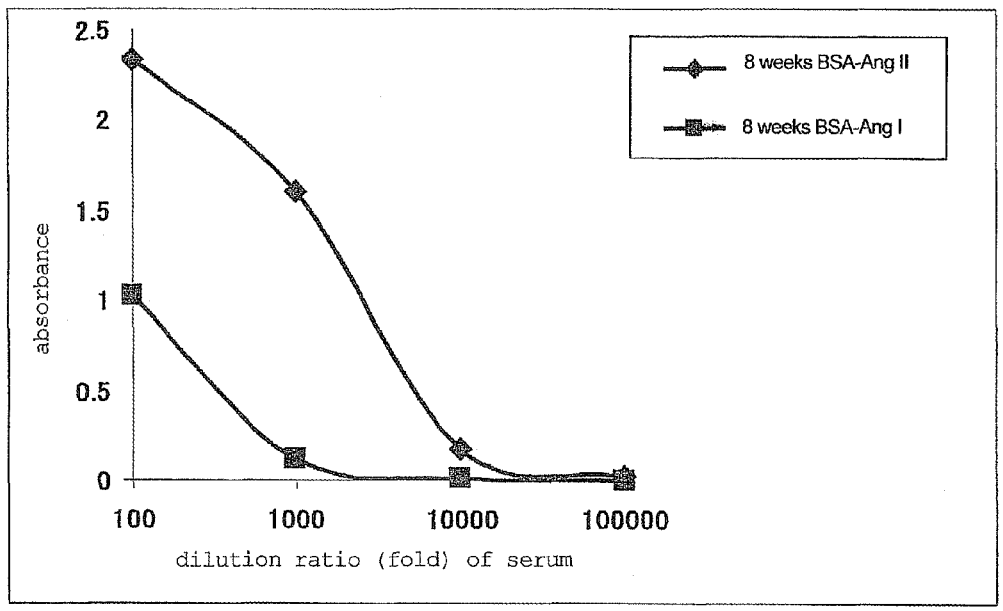
FIG. 3 shows the antibody titer at 8 week to AngI and AngII induced by HBc-AngII ISS(+) administration, wherein the vertical axis shows absorbance and the horizontal axis shows the dilution ratio of the serum.

1-2-2(b). Measurement of Antibody Titer to Angiotensin II or Angiotensin I in Serum by ELISA Method
(Method)
Angiotensin II-BSA, Angiotensin I-BSA and Angiotensinogen were respectively added to a 96 well plate by 50 µl at a concentration of 10 µg/ml, and incubated at 4° C. overnight. Thereafter, the content of the well was discarded, 3% skim milk (150 µl/well) was added and incubated for 2 hr at room temperature for blocking.
The content of the well was discarded, the mouse serum diluted with 3% skim milk was added by 50 µl each and incubated at 4° C. overnight.
Each well was washed 5 times with PBS-T. HRP-conjugated anti-mouse IgG secondary antibody or HRP-conjugated anti-rat IgG secondary antibody diluted 1/1000-fold with 3% skim milk was added (50 µl/well), and incubated for 3 hr at room temperature. The content of the well was discarded, and each well was washed 3 times with PBS-T. TMB solution (50 µl/well) was added and incubated for 30 min at room temperature. The reaction was stopped by the addition of $0.5N\ H_2SO_4$ (50 µl/well), and the absorbance was measured at 450 nm.
(Results)
The antibody titer to BSA-AngII, which was not observed before vaccine administration, increased by the total 3 times of vaccine administration (0 week and 2, 4 weeks). The antibody titer increased the highest at the time point of 8 weeks after the 3-time administration, and was maintained for 16 weeks though on decreasing tendency (FIG. 2). The antibody titer to BSA-AngII more strongly increased than to BSA-AngI by the HBc-AngII vaccine administration (FIG. 3).

2. Summary

The above blood pressure measurement and antibody titer measurement results suggest that HBc-AngII ISS(+)DNA vaccine administration can increase the antibody titer to AngII, and prevent or treat hypertension.

Example 2

1. Animal Experiment

In the same manner as in Example 1, each vector was administered 3 times (100 µg/µl×2 sites/time) to the back skin of 10-week-old hypertension rat (SHR) every 2 weeks using ShimaJET (trade name, SHIMADZU CORPORATION).
HBc-AngII ISS(+) group: 6 rats
HBc ISS(+) group: 4 rats
saline group: 5 rats
Administered at 0 week, 2 weeks, 4 weeks, and the blood pressure measurement, serum collection and antibody titer measurement were performed at 0 week, 4 weeks, 8 weeks, 12 weeks, 16 weeks, 20 weeks and 24 weeks from the start of the administration.

Figure 4:
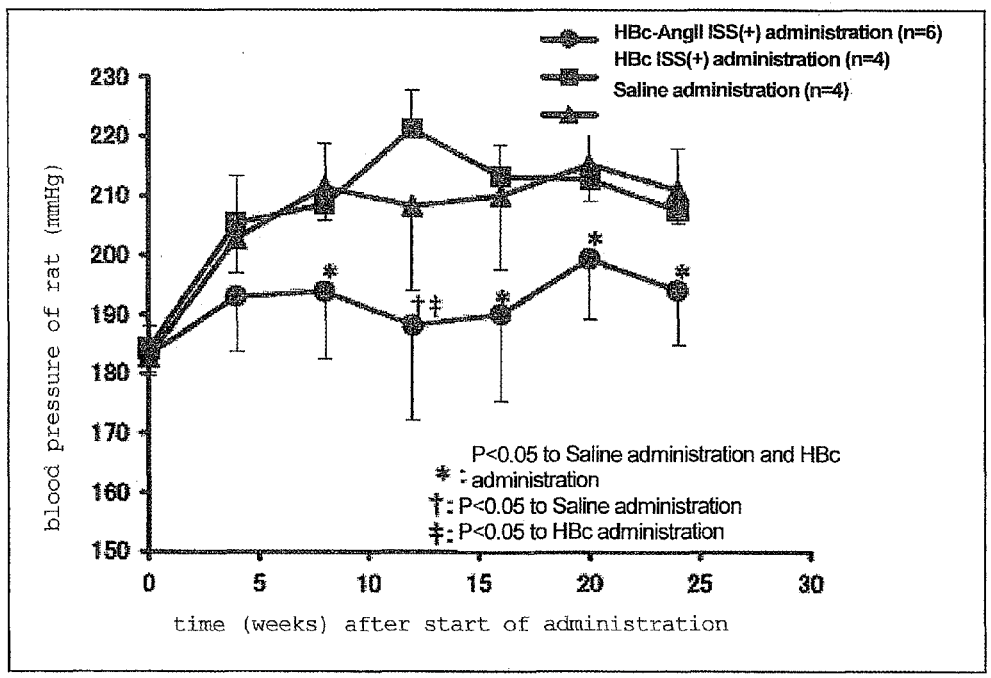
FIG. 4 shows the effect of HBc-AngII ISS(+) administration on hypertension, wherein the vertical axis shows the rat blood pressure (mmHg) and the horizontal axis shows the time (weeks) after the start of the administration.

2. Blood Pressure Measurement by Tail-Cuff Method (Method)
In the same manner as in Example 1, the blood pressure measurement was performed by a tail-cuff method. The measurement was performed 5-15 times per animal, and an average thereof was used.
(Results)
The HBc ISS(+) group (control) and saline group showed an increase in the blood pressure of SHR rats. On the other hand, HBc-AngII ISS(+) group showed a obvious decrease in the blood pressure (FIG. 4). This blood pressure decreasing effect lasted until after 24 weeks from the start of the administration.

3(a). ELISA Method (Reagent and Measurement Device)
Angiotensin II-BSA conjugate, Angiotensin I-BSA conjugate: prepared using DSS (Disuccinimidyl suberate) as a spacer
Angiotensinogen (Human): sigma A2562
Nunc Maxisorp (Cat. 442404)
5% skim milk (PBS dilution)
PBS-T (0.05% Tween)

secondary antibody: HRP-conjugated anti-mouse IgG secondary antibody (GE, NA931V), HRP-conjugated anti-rat IgG secondary antibody (GE, NA935V)
TMB solution: sigma T0440
stop solution: 0.5N $H_2SO_4$
microplate reader (Bio-Rad Inc, Japan)

3(b). Measurement of Antibody Titer to Angiotensin II in Serum by ELISA Method (Method)

Angiotensin II-BSA, Angiotensin I-BSA and Angiotensinogen were respectively added to a 96 well plate by 50 μl at a concentration of 10 μg/ml, and incubated at 4° C. overnight. Thereafter, the content of the well was discarded, 5% skim milk (150 μl/well) was added and incubated for 2 hr at room temperature for blocking.

The content of the well was discarded, the mouse serum diluted with 5% skim milk was added by 50 μl each and incubated at 4° C. overnight.

Each well was washed 5 times with PBS-T. HRP-conjugated anti-mouse IgG secondary antibody or HRP-conjugated anti-rat IgG secondary antibody diluted 1/1000-fold with 5% skim milk was added (50 μl/well) and incubated for 3 hr at room temperature. The content of the well was discarded, and each well was washed 3 times with PBS-T. TMB solution (50 μl/well) was added and incubated for 30 min at room temperature. The reaction was stopped by the addition of 0.5N $H_2SO_4$ (50 μl/well), and the absorbance was measured at 450 nm.

(Results)

Figure 5:
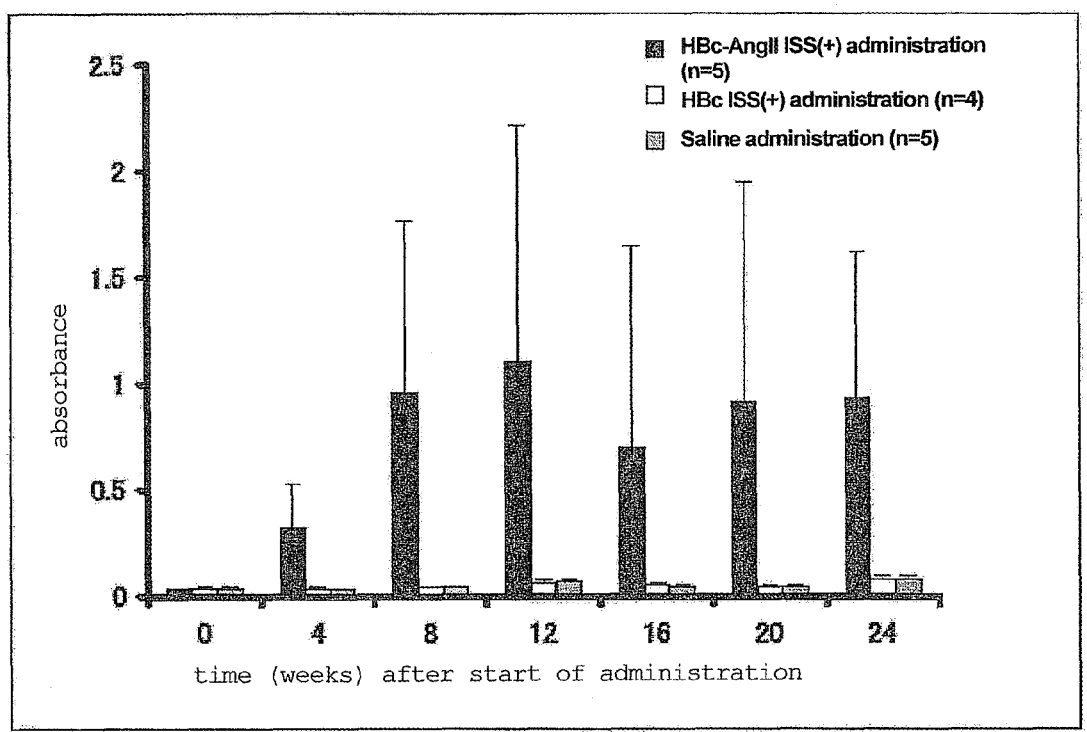
FIG. 5 shows time-course changes of the antibody titer to AngII induced by HBc-AngII ISS(+) administration, wherein the vertical axis shows absorbance and the horizontal axis shows the time (weeks) after the start of the administration.

The antibody titer to BSA-AngII, which was not observed before vaccine administration, increased by the total 3 times of vaccine administration (0 week and 2, 4 weeks). An increase in the antibody titer was detected at 4 weeks from the start of the administration. The increase in the antibody titer was maintained even after 24 weeks from the start of the administration (FIG. 5).

4. Summary

The above suggests that HBc-AngII ISS(+)DNA vaccine administration can increase the antibody titer to AngII, and prevent or treat hypertension.

INDUSTRIAL APPLICABILITY

A superior vaccine for lifestyle-related diseases such as hypertension, hyperlipidemia and the like is provided.

This application is based on patent application No. 2011-091493 filed in Japan (filing date: Apr. 15, 2011) and patent application No. 2011-227320 filed in Japan (filing date: Oct. 14, 2011), the contents of which are incorporated in full herein.

The invention claimed is:

1. A method for the treatment or improvement of hypertension in a mammal, comprising inducing production of a neutralizing antibody to angiotensin II (AngII) by administering an effective amount of an expression vector encoding a chimeric Hepatitis B virus core antigen polypeptide inserted with an amino acid sequence comprising a specific epitope of AngII to the mammal, wherein the amino acid sequence comprising the specific epitope is inserted between the amino acid residues 80 and 81 of the hepatitis B virus core antigen polypeptide.

2. A method for the treatment or improvement of hypertension in a mammal, comprising inducing production of a neutralizing antibody to angiotensin II (AngII) by administering an effective amount of an expression vector encoding a chimeric Hepatitis B virus core antigen polypeptide inserted with the amino acid sequence shown by SEQ ID NO: 16 to the mammal, wherein the amino acid sequence is inserted between the amino acid residues 80 and 81 of the hepatitis B virus core antigen polypeptide.

3. The method according to claim 1, wherein an immunostimulatory sequence (ISS) is incorporated into the expression vector.

4. The method according to claim 3, wherein the immunostimulatory sequence (ISS) consists of the nucleotide sequence shown by SEQ ID NO: 22.

5. The method according to claim 1, wherein the expression vector is administered using a needleless injector.

6. The method according to claim 5, wherein the expression vector is administered subcutaneously.

7. The method according to claim 5, wherein the needleless injector is a pressure injector.

8. The method according to claim 1, wherein the expression vector is administered plural times.

9. The method according to claim 8, wherein the administration number is 2 or 3.

10. The method according to claim 8, wherein the administration number is 3.

11. The method according to claim 1, wherein the expression vector is administered 3 times at 2-week intervals.

\* \* \* \* \*